(12) United States Patent
Ulmer et al.

(10) Patent No.: US 7,041,281 B2
(45) Date of Patent: May 9, 2006

(54) NATURAL FEEL POLYMERS

(75) Inventors: Herbert Ulmer, Hoboken, NJ (US); Timothy Gillece, Pompton Plains, NJ (US); John Katirgis, West Caldwell, NJ (US)

(73) Assignee: ISP Investments Inc., Wilmington, DE (US)

( * ) Notice: Subject to any disclaimer, the term of this patent is extended or adjusted under 35 U.S.C. 154(b) by 616 days.

(21) Appl. No.: 10/233,838

(22) Filed: Aug. 30, 2002

(65) Prior Publication Data

US 2004/0042989 A1 Mar. 4, 2004

(51) Int. Cl.
*A61K 31/785* (2006.01)
*A61K 31/795* (2006.01)
*A61K 31/77* (2006.01)
*A61K 31/765* (2006.01)
*A61K 31/80* (2006.01)

(52) U.S. Cl. ............... 424/78.36; 424/78.32; 424/78.33; 424/78.37; 424/78.38

(58) Field of Classification Search ......... 424/400, 424/78.36, 78.32, 78.33, 78.37
See application file for complete search history.

*Primary Examiner*—Thurman K. Page
*Assistant Examiner*—David L. Vanik
(74) *Attorney, Agent, or Firm*—Walter Katz; William J. Davis

(57) ABSTRACT

Natural feel polymers exhibit an advantageous blend of flexibility and a strong affinity to natural fibers imparting a natural feel when applied to keratin-based fibers, e.g. hair, skin, or textiles, e.g. cotton, wool, and are water-soluble and water-resistant. The polymers include repeat units of a monomer (e.g. α-olefin) maleic anhydride alkyl half-ester or full acid, maleamic acid and maleimide, which are derivatized with a polyether amine.

9 Claims, No Drawings

NATURAL FEEL POLYMERS

CROSS-REFERENCE TO RELATED U.S. PATENTS

This application is related to U.S. Pat. Nos. 5,869,695; 5,886,194; 5,959,122; 5,994,385; and 6,025,501, assigned to the same assignee as herein, which describe hair styling polymers containing derivatized maleimide repeat units.

BACKGROUND OF THE INVENTION

1. Field of the Invention

This invention relates to polymers useful in personal care products, and, particularly to hair styling polymers, referred to herein as "natural feel" polymers, which possess the desirable physical attributes of flexibility and a smooth feel, as well as water-solubility and water-resistance. Though water-solubility is preferred it is not necessary, but depends on the final end product application.

2. Description of the Prior Art

Hair styling polymers which feel stiff on hair are rather brittle under a high applied stress; accordingly, these polymers will shatter easily when strained appreciably. On the other hand, highly flexible polymers when used in hair styling will bend under both high and low stress but they are generally considered by the user to be too soft for desirable hair styling.

Accordingly, it is an object of this invention to provide polymers which have the desirable attributes of stiffness and flexibility, and have a strong affinity for hair imparting a natural feel for the user, and are also water-soluble and water-resistant.

Another object herein is to provide natural feel polymers which can be easily removed from a substrate such as hair or skin, or a textile fiber, by simple washing.

These and other objects and features of the invention will be made apparent from the following description thereof.

SUMMARY OF THE INVENTION

Natural feel polymers have defined amounts of repeat units of
(a) a monomer (e.g. α-olefin) -maleic anhydride alkyl half-ester or full acid,
(b) maleamic acid, and (c) a maleimide, as shown below:

NATURAL FEEL POLYMERS

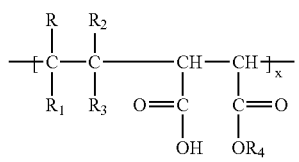

(a) half-ester or full ester

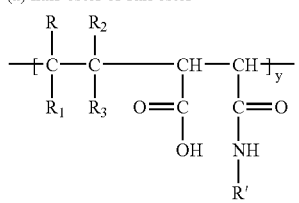

(b) maleamic acid

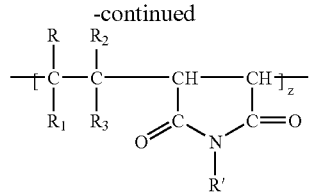

(c) maleimide where:
$R$, $R_1$, $R_2$ and $R_3$ are selected from H, alkyl, alkoxy, cycloalkyl, aryl, ester, acid, hydroxy, hydroxyalkyl, amido, fluoro, halo and silyl, and $R_4$ is H or alkyl; and R' is a derivatizing group selected from X, a hydrophobic amine; Y, a hydrophilic amine; and Z, a polyether amine; and suitable mixtures thereof;

x, y and z are present, in mole %, of 0–99.9, 0–50 and 0.1–100, respectively; preferably 0–50, 0–5 and 50–100; and X, Y and Z are present in mole ratios of 0–20:0–99:0.1–20; preferably, 0–10:40–98:1–10.

DETAILED DESCRIPTION OF THE INVENTION

The natural feel polymers of the present invention are particularly characterized by repeat units which contain an abundance (by weight) of polyether amine derivatizing groups which can hydrogen-bond with itself or other repeat units in the polymer to form an intra- or inter-molecular polymer resulting in a pseudo-network polymer. This polymer thus acts as if it is crosslinked. Cohesion between such hydrogen-bonded molecules provides the polymer with water-resistance, but also with water solubility because, once the polymer is flooded with water, it will admit sufficient amount of water for solubilization. The polymers show good adhesion to natural substrates but can be removed easily if desired. Some polyether derivatizers may also crystallize upon dry-down, resulting in enhanced properties such as water resistance.

Representative structural components of the natural feel polymers of the invention are given below.
Reactants for Natural Feel Polymers
Polymer Backbone
  Monomer-Maleic Anhydride Copolymer
  Alkyl vinyl ether-maleic anhydride copolymer, e.g. methyl vinyl ether-maleic anhydride copolymer, or isobutyl vinyl ether-maleic anhydride copolymer; and derivatives thereof, including alpha-olefin-maleic anhydride copolymer, e.g. ethylene-maleic anhydride copolymer, or isobutylene-maleic anhydride copolymer; styrene-maleic anhydride copolymer, etc.
Derivatizers
  Hydrophobic Amine (X)
  Monofunctional α-unsubstituted primary or secondary monoamines, unsubstituted or substituted with alkyl, aryl, heterocyclic, aromatic, fluoro, silyl amino, carboxy and halogen; e.g. $C_1$–$C_{40}$ alkyl $NH_2$; butylamine, isobutyl amine, and octadecylamine. These amines may be included in the polymer to alter the solubility of the polymer.
  Hydrophilic Amine (Y)
  Hydroxy α-unsubstituted amines e.g. ethanolamine, isopropylamine, n-propanolamine, 3-amino-1-propanol; methoxyethyl amine, and diglycol amine; and alkyl diamines, e.g. 3-(dimethylamino)propylamine, dimethylethylene diamine, N-aminopropyl pyrrolidone, N-aminoethyl pyrrolidone, and 1-(3-aminopropyl)imidazole. These amines are included in the polymer to modify the adhesive/cohesive balance in the polymer, and to increase compatability with other components in system.

Polyether Amine (Z)
Polyoxyalkylene amine, having the formula:

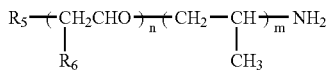

where $R_5$ and $R_6$ are selected from H and alkyl; e.g. $R_5$ is $CH_3$ and $R_6$ is H; and $R_5$ is $CH_3$ and $R_6$ is $CH_3$; and n and m are integers from 1–50; e.g. n=32 and m=10. These amines are obtainable as Jeffamine® M Monoamines (Huntsman Corp), with various molecular weights and ethylene oxide (EO)/propylene oxide (PO) ratios. These amines are present to provide natural feel properties in the polymer, i.e. softness and flexibility, as well as the desired adhesive/cohesive balance.

The invention will now be described with reference to the following examples.

EXAMPLE 1

The following were charged into a 2-liter, stainless steel high pressure reactor.

| | |
|---|---|
| P(maleic anhydride/isobutene) (Man) | 72.94 g |
| 3-(dimethylamino) propylamine (50 mol % based on Man) | 24.17 g |
| Jeffamine ® M-2070 (2 mol % based on Man) (M.W. 2,000, 70/30 EO/PO) (water soluble) | 20.73 g |
| Triethylamine (43 mol % based on Man) (Neutralizer) | 20.59 g |
| Methanol | 257.07 g |

The reactor was sealed, purged 3 times with $N_2$ gas, and heating was begun according to the following heating profile.

Ambient→90° C., 1½ hr.
90° C.→90° C., 2 hr.
90° C.→130° C., 1½ hr.
130° C.→130° C., 8 hr.
130° C.→35° C., 1 hr.

At the end of the heating cycle, the polymer product was obtained as a lightly viscous, yellow, clear solution; then it was flooded with water to give a viscous, hazy, yellow-colored solution. The solution was mixed with neutralized Carbopol® in an amount present in a typical styling gel formulation. A thick, clear gel was obtained after an hour. The gel formulation was applied to hair and the resultant film was stressed. The film showed a natural feel, combining firm and flexible characteristics, water-resistance and water-solubility, and excellent high humidity curl retention.

EXAMPLE 2

The following reactants were added to a 2-liter pressure reactor:

| | |
|---|---|
| Poly(isobutylene/maleic anhydride) | 119.22 g |
| Dimethylaminopropylamine | 39.51 g |
| Jeffamine M-2005 (M.W. 2,000, 5/95 EO/PO) (water-insoluble) | 42.35 g |
| Jeffamine M-2070 (M.W. 2,000, 70/30 EO/PO) (water-soluble) | 42.35 g |
| Triethylamine | 31.30 g |
| Ethanol | 510.20 g |

The reactor was sealed and purged with an inert gas. The following heating profile was initiated:

| | |
|---|---|
| Heat to 125° C. - | 4 hours |
| Hold at 125° C. - | 12 hours |
| Cool to 35° C. - | 1 hour |

After the heating profile was complete, the polymer solution was discharged from the reactor. The resultant material was a viscous, clear yellow solution. This material was laid down as a film and allowed to dry. A non-brittle film resulted which was water soluble. Exchanging water for ethanol gave a water-based solution having similar properties to the ethanol-based material.

EXAMPLE 3

The following reactants were added to a 2-liter pressure reactor:

| | |
|---|---|
| Poly(isobutylene/maleic anhydride) | 119.22 g |
| Dimethylaminopropylamine | 39.51 g |
| Jeffamine M-2005 | 84.70 g |
| Triethylamine | 31.30 g |
| Ethanol | 510.20 g |

The reactor was sealed and purged with an inert gas. The following heating profile was initiated:

| | |
|---|---|
| Heat to 125° C. - | 4 hours |
| Hold at 125° C. - | 12 hours |
| Cool to 35° C. - | 1 hour |

After the heating profile was complete, the polymer solution was discharged from the reactor. The resultant product was a viscous, clear yellow solution. This material was laid down as a film and allowed to dry. A non-brittle film resulted. Exchanging with water gave a water-based solution having similar properties to the ethanol-based material.

EXAMPLE 4

The following reactants were added to a 2-liter pressure reactor:

| | |
|---|---|
| Poly(isobutylene/maleic anhydride) | 119.22 g |
| Dimethylaminopropylamine | 39.51 g |
| Jeffamine M-2005 | 84.70 g |
| Jeffamine M-2070 | 33.90 g |
| Triethylamine | 31.30 g |
| Ethanol | 573.17 g |

The reactor was sealed and purged with an inert gas. The following heating profile was initiated:

| | |
|---|---|
| Heat to 125° C. - | 4 hours |
| Hold at 125° C. - | 12 hours |
| Cool to 35° C. - | 1 hour |

After the heating profile was complete, the polymer solution was discharged from the reactor. The resultant material was a viscous clear yellow solution. This material, when laid down as a film and allowed to dry, resulted in a flexible film. This same material can be exchanged with water to give a water-based solution having similar properties to the ethanol-based material.

EXAMPLE 5

The following reactants were added to a 2-liter pressure reactor:

| | |
|---|---|
| Poly(isobutylene/maleic anhydride) | 119.22 g |
| Dimethylaminopropylamine | 39.51 g |
| Jeffamine M-2005 | 101.70 g |
| Jeffamine M-2070 | 84.70 g |
| Triethylamine | 31.30 g |
| Ethanol | 699.08 g |

The reactor was sealed and purged with an inert gas. The following heating profile was initiated:

| | |
|---|---|
| Heat to 125° C. - | 4 hours |
| Hold at 125° C. - | 12 hours |
| Cool to 35° C. - | 1 hour |

After the heating profile was complete, the polymer solution was discharged from the reactor. The resultant material was a viscous clear yellow solution. This material, when laid down as a film and allowed to dry, resulted in a very-flexible film. This same material can be exchanged with water to give a water-based solution having similar properties to the ethanol-based material.

The natural feel polymers of Examples 1–5 were formulated into typical hair care products designed for use in the modes of styling, mousse, gel and spray hair care products. These products performed well in practice giving the user the advantages of the natural feel polymers therein, particularly a firm and flexible characteristic, water-resistance and water-solubility, and excellent high humidity curl retention.

While the invention has been described with particular reference to certain embodiments thereof, it will be understood that changes and modifications may be made which are within the skill of the art. Accordingly, it is intended to be bound only by the following claims, in which:

What is claimed is:

1. A natural feel polymer which shows an advantageous blend of stiffness and flexibility, a strong affinity to natural fibers, water-solubility and water-resistance, characterized structurally by repeat units of (a) a monomer-maleic anhydride alkyl half-ester or full acid, (b) maleamic acid, and (c) maleimide, of the formulas:

$$-\left[\begin{array}{c}R\\|\\C\\|\\R_1\end{array}-\begin{array}{c}R_2\\|\\C\\|\\R_3\end{array}-\begin{array}{c}CH\\|\\O=C\\|\\OH\end{array}-\begin{array}{c}CH\\|\\C=O\\|\\OR_4\end{array}\right]_x-$$

(a) half-ester or full ester $$-\left[\begin{array}{c}R\\|\\C\\|\\R_1\end{array}-\begin{array}{c}R_2\\|\\C\\|\\R_3\end{array}-\begin{array}{c}CH\\|\\O=C\\|\\OH\end{array}-\begin{array}{c}CH\\|\\C=O\\|\\NH\\|\\R'\end{array}\right]_y-$$

(b) maleamic acid $$-\left[\begin{array}{c}R\\|\\C\\|\\R_1\end{array}-\begin{array}{c}R_2\\|\\C\\|\\R_3\end{array}-\begin{array}{c}CH\\|\\C\\\diagup\\O\end{array}-\begin{array}{c}CH\\|\\C=O\\\diagup\\N\\|\\R'\end{array}\right]_z-$$

(c) maleimide where:

R, $R_1$, $R_2$ and $R_3$ are selected from H, alkyl, alkoxy, cycloalkyl, aryl, ester, acid, hydroxy, hydroxyalkyl, amido, fluoro, halo and silyl, and $R_4$ is H or alkyl; and R' is a polyoxyalkylene amine, having the formula:

$$R_5-(CH_2CHO)_n-(CH_2-CH)_m-NH_2$$
$$\phantom{R_5-(CH_2C}|\phantom{HO)_n-(CH_2-}|$$
$$\phantom{R_5-(CH_2CH}R_6\phantom{O)_n-(CH_2-}CH_3$$

where $R_5$ and $R_6$ are selected from H and alkyl; and n and m are integers from 1–50; wherein:

x, y and z are present, in mole %, of 0–99.9, 0–50 and 0.1–100, respectively.

2. A natural feel polymer according to claim 1 wherein x=0–50, y=0–5 and z=5–100.

3. A natural feel polymer according to claim 1 wherein $R_5$ is $CH_3$ and $R_6$ is H.

4. A natural feel polymer according to claim 1 wherein both $R_5$ and $R_6$ are $CH_3$.

5. A natural feel polymer according to claim 1 wherein n=32 and m=10.

6. A natural feel polymer according to claim 1 wherein, in (a), said monomer is an α-olefin.

7. A personal care formulation including the natural feel polymer of claim 1.

8. A personal care formulation according to claim 7 which is a hair care product.

9. A hair care formulation according to claim 8 which is a styling, mousse, gel or spray hair care formulation.

* * * * *